US008124814B2

(12) United States Patent
Krafft et al.

(10) Patent No.: US 8,124,814 B2
(45) Date of Patent: Feb. 28, 2012

(54) CRUDE GLYCEROL-BASED PRODUCT, PROCESS FOR ITS PURIFICATION AND ITS USE IN THE MANUFACTURE OF DICHLOROPROPANOL

(75) Inventors: Philippe Krafft, Rhode Saint Genese (BE); Patrick Gilbeau, Braine-le-Comte (BE); Dominique Balthasart, Brussels (BE)

(73) Assignee: Solvay (Societe Anonyme), Brussels (BE)

( * ) Notice: Subject to any disclaimer, the term of this patent is extended or adjusted under 35 U.S.C. 154(b) by 119 days.

(21) Appl. No.: 12/304,391

(22) PCT Filed: Jun. 12, 2007

(86) PCT No.: PCT/EP2007/055742
§ 371 (c)(1),
(2), (4) Date: Dec. 11, 2008

(87) PCT Pub. No.: WO2007/144335
PCT Pub. Date: Dec. 21, 2007

(65) Prior Publication Data
US 2009/0198041 A1 Aug. 6, 2009

(30) Foreign Application Priority Data

Jun. 14, 2006 (FR) ..................... 06 05325
Mar. 15, 2007 (FR) ..................... 07 53863

(51) Int. Cl.
*C07C 31/34* (2006.01)
(52) U.S. Cl. ....................................................... 568/844
(58) Field of Classification Search .................. 568/844
See application file for complete search history.

(56) References Cited

U.S. PATENT DOCUMENTS 280,893 A 7/1883 Baujard
(Continued)

FOREIGN PATENT DOCUMENTS

CN 1296003 A 5/2001
(Continued)

OTHER PUBLICATIONS

Gibson, The Preparation, Properties, and Uses of Glycerol Derivatives. Part III. The Chlorohydrins, Chemistry and Industry, 1931, 12 pages.*

(Continued)

*Primary Examiner* — Paul A Zucker
(74) *Attorney, Agent, or Firm* — Oblon, Spivak, McClelland, Maier & Neustadt, L.L.P.

(57) ABSTRACT

The invention relates to a crude glycerol-based product comprising glycerol alkyl ethers, to a purification process comprising a treatment of evaporative concentration, of evaporative crystallization, of distillation, of fractional distillation, of stripping, or of liquid-liquid extraction and to the use of the purified product in the manufacture of dichloropropanol.

17 Claims, No Drawings

U.S. PATENT DOCUMENTS

| | | |
|---|---|---|
| 865,727 A | 9/1907 | Queneau |
| 2,060,715 A | 11/1936 | Arvin |
| 2,063,891 A | 12/1936 | Dreyfus |
| 2,144,612 A | 1/1939 | Britton et al. |
| 2,198,600 A | 4/1940 | Britton et al. |
| 2,248,635 A | 7/1941 | Marple et al. |
| 2,319,876 A | 5/1943 | Moss |
| 2,444,333 A | 6/1948 | Castan |
| 2,505,735 A | 4/1950 | Halbedel |
| 2,726,072 A | 12/1955 | Herman |
| 2,811,227 A | 10/1957 | O'Connor |
| 2,829,124 A | 4/1958 | Napravnik et al. |
| 2,860,146 A | 11/1958 | Furman et al. |
| 2,876,217 A | 3/1959 | Paschall |
| 2,945,004 A | 7/1960 | Greenlee |
| 2,960,447 A | 11/1960 | Anderson et al. |
| 3,026,270 A | 3/1962 | Robinson, Jr. |
| 3,052,612 A | 9/1962 | Henegar et al. |
| 3,061,615 A | 10/1962 | Viriot et al. |
| 3,121,727 A | 2/1964 | Baliker et al. |
| 3,135,705 A | 6/1964 | Vandenberg |
| 3,158,580 A | 11/1964 | Vandenberg |
| 3,158,581 A | 11/1964 | Vandenberg |
| 3,247,227 A | 4/1966 | White |
| 3,260,059 A | 7/1966 | Rosenberg et al. |
| 3,341,491 A | 9/1967 | Robinson et al. |
| 3,355,511 A | 11/1967 | Schwarzer |
| 3,385,908 A | 5/1968 | Schwarzer |
| 3,445,197 A | 5/1969 | Resh et al. |
| 3,457,282 A | 7/1969 | Polak et al. |
| 3,618,295 A | 11/1971 | Geiger et al. |
| 3,711,388 A | 1/1973 | Gritzner |
| 3,766,221 A | 10/1973 | Becker |
| 3,839,169 A | 10/1974 | Moyer |
| 3,865,886 A | 2/1975 | Schindler et al. |
| 3,867,166 A | 2/1975 | Sullivan |
| 3,954,581 A | 5/1976 | Carlin |
| 3,968,178 A | 7/1976 | Obrecht et al. |
| 4,003,723 A | 1/1977 | Schafer et al. |
| 4,011,251 A | 3/1977 | Tjurin et al. |
| 4,024,301 A | 5/1977 | Witenhafer et al. |
| 4,127,594 A | 11/1978 | Anderson et al. |
| 4,173,710 A | 11/1979 | Boulet et al. |
| 4,197,399 A | 4/1980 | Noel et al. |
| 4,220,529 A | 9/1980 | Daude-Lagrave |
| 4,240,885 A | 12/1980 | Suciu et al. |
| 4,255,470 A | 3/1981 | Cohen et al. |
| 4,294,776 A | 10/1981 | Hardy et al. |
| 4,390,680 A | 6/1983 | Nelson |
| 4,405,465 A | 9/1983 | Moore et al. |
| 4,415,460 A | 11/1983 | Suciu et al. |
| 4,464,517 A | 8/1984 | Makino et al. |
| 4,499,255 A | 2/1985 | Wang et al. |
| 4,595,469 A | 6/1986 | Foller |
| 4,609,751 A | 9/1986 | Hajjar |
| 4,634,784 A | 1/1987 | Nagato et al. |
| 4,655,879 A | 4/1987 | Brockmann et al. |
| 4,935,220 A | 6/1990 | Schneider et al. |
| 4,960,953 A | 10/1990 | Jakobson et al. |
| 4,973,763 A | 11/1990 | Jakobson et al. |
| 4,990,695 A | 2/1991 | Buenemann et al. |
| 5,041,688 A | 8/1991 | Jakobson et al. |
| 5,200,163 A | 4/1993 | Henkelmann et al. |
| 5,278,260 A | 1/1994 | Schaffner et al. |
| 5,286,354 A | 2/1994 | Bard et al. |
| 5,344,945 A | 9/1994 | Grunchard |
| 5,359,094 A | 10/1994 | Teles et al. |
| 5,393,428 A | 2/1995 | Dilla et al. |
| 5,445,741 A | 8/1995 | Dilla et al. |
| 5,478,472 A | 12/1995 | Dilla et al. |
| 5,486,627 A | 1/1996 | Quarderer, Jr. et al. |
| 5,567,359 A | 10/1996 | Cassidy et al. |
| 5,578,740 A | 11/1996 | Au et al. |
| 5,679,839 A | 10/1997 | Armand et al. |
| 5,710,350 A | 1/1998 | Jeromin et al. |
| 5,731,476 A | 3/1998 | Shawl et al. |
| 5,744,655 A | 4/1998 | Thomas et al. |
| 5,779,915 A | 7/1998 | Becker et al. |
| 5,908,946 A | 6/1999 | Stern et al. |
| 5,993,974 A | 11/1999 | Fukushima et al. |
| 6,103,092 A | 8/2000 | Silva |
| 6,111,153 A | 8/2000 | Crow et al. |
| 6,142,458 A | 11/2000 | Howk |
| 6,177,599 B1 | 1/2001 | Cowfer et al. |
| 6,270,682 B1 | 8/2001 | Santen et al. |
| 6,288,248 B1 | 9/2001 | Strebelle et al. |
| 6,288,287 B2 * | 9/2001 | Ueoka et al. ............. 568/869 |
| 6,350,888 B1 | 2/2002 | Strebelle et al. |
| 6,350,922 B1 | 2/2002 | Vosejpka et al. |
| 6,521,794 B2 | 2/2003 | Hirota |
| 6,719,957 B2 | 4/2004 | Brady, Jr. et al. |
| 6,740,633 B2 | 5/2004 | Norenberg et al. |
| 6,831,201 B2 | 12/2004 | Katsuura et al. |
| 7,126,032 B1 | 10/2006 | Aiken |
| 7,128,890 B2 | 10/2006 | Ollivier |
| 7,557,253 B2 | 7/2009 | Gilbeau |
| 7,584,629 B2 | 9/2009 | Sohn et al. |
| 7,615,670 B2 | 11/2009 | Gilbeau |
| 2001/0014763 A1 | 8/2001 | Ueoka et al. |
| 2003/0209490 A1 | 11/2003 | Camp et al. |
| 2004/0016411 A1 | 1/2004 | Joyce et al. |
| 2004/0024244 A1 | 2/2004 | Walsdorff et al. |
| 2004/0047781 A1 | 3/2004 | Becenel, Jr. |
| 2004/0150123 A1 | 8/2004 | Strofer et al. |
| 2004/0179987 A1 | 9/2004 | Oku et al. |
| 2004/0232007 A1 | 11/2004 | Carson et al. |
| 2005/0115901 A1 | 6/2005 | Heuser et al. |
| 2005/0261509 A1 | 11/2005 | Delfort et al. |
| 2006/0052272 A1 | 3/2006 | Meli et al. |
| 2006/0079433 A1 | 4/2006 | Hecht et al. |
| 2006/0123842 A1 | 6/2006 | Sohn et al. |
| 2007/0112224 A1 | 5/2007 | Krafft et al. |
| 2007/0293707 A1 | 12/2007 | Wolfert et al. |
| 2008/0053836 A1 | 3/2008 | Bulan et al. |
| 2008/0146753 A1 | 6/2008 | Woike et al. |
| 2008/0154050 A1 | 6/2008 | Gilbeau |
| 2008/0161613 A1 | 7/2008 | Krafft et al. |
| 2008/0194847 A1 | 8/2008 | Krafft et al. |
| 2008/0194849 A1 | 8/2008 | Krafft et al. |
| 2008/0194851 A1 | 8/2008 | Gilbeau |
| 2008/0200642 A1 | 8/2008 | Krafft |
| 2008/0200701 A1 | 8/2008 | Krafft et al. |
| 2008/0207930 A1 | 8/2008 | Gilbeau et al. |
| 2008/0214848 A1 | 9/2008 | Krafft et al. |
| 2008/0281132 A1 | 11/2008 | Krafft et al. |
| 2009/0022653 A1 | 1/2009 | Strebelle et al. |
| 2009/0131631 A1 | 5/2009 | Krafft et al. |
| 2009/0173636 A1 | 7/2009 | Ooms et al. |
| 2009/0198041 A1 | 8/2009 | Krafft et al. |
| 2009/0270588 A1 | 10/2009 | Krafft et al. |
| 2009/0275726 A1 | 11/2009 | Krafft et al. |
| 2010/0029959 A1 | 2/2010 | Fan et al. |

FOREIGN PATENT DOCUMENTS

| | | |
|---|---|---|
| CN | 101041421 | 9/2007 |
| DE | 58396 C | 8/1891 |
| DE | 180668 C | 1/1906 |
| DE | 197308 C | 11/1906 |
| DE | 238341 C | 3/1908 |
| DE | 197309 C | 4/1908 |
| DE | 869 193 | 3/1953 |
| DE | 1041488 B | 10/1958 |
| DE | 1075103 B | 2/1960 |
| DE | 1226554 B | 10/1966 |
| DE | 2 241 393 | 2/1974 |
| DE | 25 21 813 | 12/1975 |
| DE | 3003819 A1 | 8/1981 |
| DE | 3243617 | 5/1984 |
| DE | 216471 A1 | 12/1984 |
| DE | 3721003 C1 | 12/1988 |
| DE | 43 02 306 | 8/1994 |
| DE | 43 35 311 | 4/1995 |
| DE | 10203914 C1 | 10/2003 |
| DE | 10254709 A1 | 6/2004 |
| EP | 0 296 341 | 12/1988 |
| EP | 0347618 A2 | 12/1989 |
| EP | 0358255 A1 | 3/1990 |

| | | | | | | |
|---|---|---|---|---|---|---|
| EP | 0421379 A1 | 4/1991 | | JP | 62242638 A | 10/1987 |
| EP | 0 452 265 | 10/1991 | | JP | 63195288 A | 8/1988 |
| EP | 0518765 A1 | 12/1992 | | JP | 2-137704 | 5/1990 |
| EP | 0522382 A1 | 1/1993 | | JP | 03014527 A | 1/1991 |
| EP | 0535949 B1 | 4/1993 | | JP | 03223267 A | 10/1991 |
| EP | 0561441 A1 | 9/1993 | | JP | 3223267 A | 10/1991 |
| EP | 0563720 A1 | 10/1993 | | JP | 04089440 A | 3/1992 |
| EP | 0568389 A1 | 11/1993 | | JP | 04-217637 | 8/1992 |
| EP | 0582201 A2 | 2/1994 | | JP | 625196 B2 | 4/1994 |
| EP | 0 618 170 | 10/1994 | | JP | 06184024 A | 7/1994 |
| EP | 0 916 624 | 5/1999 | | JP | 6321852 A | 11/1994 |
| EP | 0919551 A1 | 6/1999 | | JP | 859593 | 3/1996 |
| EP | 0 774 450 | 2/2000 | | JP | 09-299953 | 11/1997 |
| EP | 1059278 A2 | 12/2000 | | JP | 10139700 A | 5/1998 |
| EP | 1106237 A1 | 6/2001 | | JP | 1998218810 A | 8/1998 |
| EP | 1153887 A2 | 11/2001 | | JP | 2000-344692 | 12/2000 |
| EP | 1163946 A1 | 12/2001 | | JP | 2001-037469 | 2/2001 |
| EP | 1 231 189 | 8/2002 | | JP | 2001-213827 A | 8/2001 |
| EP | 1298154 A1 | 4/2003 | | JP | 2001-261308 | 9/2001 |
| EP | 1411027 A1 | 4/2004 | | JP | 2001-1261581 A | 9/2001 |
| EP | 1752435 A1 | 2/2007 | | JP | 2002-02033 A2 | 1/2002 |
| EP | 1752436 A1 | 2/2007 | | JP | 20020038195 A | 2/2002 |
| EP | 1760060 A1 | 3/2007 | | JP | 2002-265986 | 9/2002 |
| EP | 1762556 A1 | 3/2007 | | JP | 2002-363153 A | 12/2002 |
| EP | 1770081 A1 | 4/2007 | | JP | 2003-89680 A | 3/2003 |
| EP | 1772446 A1 | 4/2007 | | JP | 2003081891 A | 3/2003 |
| EP | 1775278 A1 | 4/2007 | | JP | 2005007841 A2 | 1/2005 |
| EP | 2 085 364 | 8/2009 | | JP | 2005097177 A2 | 4/2005 |
| FR | 1 306 231 | 10/1961 | | JP | 2007-008898 | 1/2007 |
| FR | 1 417 388 | 10/1964 | | JP | 2009-263338 | 11/2009 |
| FR | 1476073 A | 4/1967 | | KR | 900006513 | 11/1987 |
| FR | 1 577 792 | 8/1968 | | KR | 1019920003099 B1 | 4/1992 |
| FR | 2 180 138 | 5/1973 | | KR | 10-514819 B1 | 9/2005 |
| FR | 2 217 372 | 2/1974 | | SU | 123153 | 1/1959 |
| FR | 2565229 A1 | 12/1985 | | SU | 1125226 | 11/1984 |
| FR | 2752242 A1 | 2/1998 | | SU | 1159716 | 6/1985 |
| FR | 2862644 A1 | 5/2005 | | SU | 1685969 | 10/1991 |
| FR | 2868419 A1 | 10/2005 | | WO | WO 95/14639 | 6/1995 |
| FR | 2869612 A1 | 11/2005 | | WO | WO 96/07617 | 3/1996 |
| FR | 2869613 A1 | 11/2005 | | WO | WO 96/15980 | 5/1996 |
| FR | 2872504 A1 | 1/2006 | | WO | WO 97/48667 | 12/1997 |
| FR | 2881732 A1 | 8/2006 | | WO | WO 98/37024 | 8/1998 |
| FR | 2885903 A1 | 11/2006 | | WO | WO 99/14208 | 3/1999 |
| FR | 2 912 743 | 8/2008 | | WO | WO 9932397 A1 | 7/1999 |
| FR | 2 913 683 | 9/2008 | | WO | WO 00/24674 | 5/2000 |
| FR | 2913683 A1 | 9/2008 | | WO | WO 01/41919 | 6/2001 |
| FR | 2 917 411 | 12/2008 | | WO | WO 0186220 A2 | 11/2001 |
| FR | 2918058 A1 | 1/2009 | | WO | WO 02/26672 A2 | 4/2002 |
| FR | 2925045 A1 | 6/2009 | | WO | WO 03/064357 | 8/2003 |
| FR | 2929611 A1 | 10/2009 | | WO | WO 2004/056758 | 7/2004 |
| FR | 2935699 A1 | 3/2010 | | WO | WO 2005021476 A1 | 3/2005 |
| FR | 2935968 A1 | 3/2010 | | WO | WO 2005/054167 A1 * | 6/2005 |
| GB | 14676 A * | 0/1914 | | WO | WO 2005054167 A1 | 6/2005 |
| GB | 14767 A | 0/1914 | | WO | WO 2005/097722 | 10/2005 |
| GB | 406345 | 8/1932 | | WO | WO 2005/115954 | 12/2005 |
| GB | 404938 A | 1/1934 | | WO | WO 2005/116004 | 12/2005 |
| GB | 467481 A | 6/1937 | | WO | WO 2006020234 A1 | 2/2006 |
| GB | 541357 A | 11/1941 | | WO | WO 2006/100311 A2 | 9/2006 |
| GB | 679536 A | 9/1952 | | WO | WO 2006/100312 A2 | 9/2006 |
| GB | 702143 A | 1/1954 | | WO | WO 2006/100313 A2 | 9/2006 |
| GB | 736641 A | 9/1955 | | WO | WO 2006/100314 A1 | 9/2006 |
| GB | 799567 A | 8/1958 | | WO | WO 2006/100315 A2 | 9/2006 |
| GB | 984446 A | 2/1965 | | WO | WO 2006/100316 A1 | 9/2006 |
| GB | 984633 A | 3/1965 | | WO | WO 2006/100317 A1 | 9/2006 |
| GB | 1083594 A | 9/1967 | | WO | WO 2006/100318 A2 | 9/2006 |
| GB | 1286893 A | 8/1972 | | WO | WO 2006/100319 A1 | 9/2006 |
| GB | 1387668 A | 3/1975 | | WO | WO 2006/100320 A2 | 9/2006 |
| GB | 1 493 538 | 4/1975 | | WO | WO 2006100311 A2 | 9/2006 |
| GB | 1414976 A | 11/1975 | | WO | WO 2006100312 A2 | 9/2006 |
| GB | 2173496 A | 10/1986 | | WO | WO 2006100313 A2 | 9/2006 |
| GB | 2336584 A | 10/1999 | | WO | WO 2006100314 A1 | 9/2006 |
| HU | 2002-003023 | 3/2004 | | WO | WO 2006100315 A2 | 9/2006 |
| JP | 3927230 B2 | 11/1939 | | WO | WO 2006100316 A1 | 9/2006 |
| JP | 50-062909 | 5/1975 | | WO | WO 2006100317 A1 | 9/2006 |
| JP | 51021635 B | 7/1976 | | WO | WO 2006100318 A2 | 9/2006 |
| JP | 55041858 A | 3/1980 | | WO | WO 2006100319 A1 | 9/2006 |
| JP | 5629572 | 3/1981 | | WO | WO 2006100320 A2 | 9/2006 |
| JP | 5699432 | 8/1981 | | WO | WO 2006/106153 A2 | 10/2006 |
| JP | 61 112066 A | 5/1986 | | WO | WO 2006/106154 A1 | 10/2006 |

| | | |
|---|---|---|
| WO | WO 2006/106155 A2 | 10/2006 |
| WO | WO 2006106153 A2 | 10/2006 |
| WO | WO 2006106154 A1 | 10/2006 |
| WO | WO 2006106155 A2 | 10/2006 |
| WO | WO 2007/054505 A2 | 5/2007 |
| WO | WO 2007054505 A2 | 5/2007 |
| WO | WO 2007144335 A1 | 12/2007 |
| WO | WO 2008/101866 | 8/2008 |
| WO | WO2008/107468 | 9/2008 |
| WO | WO2008/110588 | 9/2008 |
| WO | WO2008/145729 | 12/2008 |
| WO | WO 2008/147473 | 12/2008 |
| WO | WO 2008/152043 | 12/2008 |
| WO | WO 2008/152044 | 12/2008 |
| WO | WO 2008/152045 | 12/2008 |
| WO | WO 2009/000773 | 12/2008 |
| WO | WO 2009/016149 A2 | 2/2009 |
| WO | WO 2009/026212 | 2/2009 |
| WO | WO2009/043796 A1 | 4/2009 |
| WO | WO 2009/077528 | 6/2009 |
| WO | WO 2009/077528 A1 | 6/2009 |
| WO | WO 2009/095429 | 8/2009 |
| WO | WO 2009/095429 A1 | 8/2009 |
| WO | WO2009/121853 A1 | 10/2009 |
| WO | WO 2009/121853 | 10/2009 |
| WO | WO 2010/029039 | 3/2010 |
| WO | WO 2010/029039 A1 | 3/2010 |
| WO | WO 2010/029153 | 3/2010 |
| WO | WO 2010/029153 A1 | 3/2010 |
| WO | WO 2010/066660 | 6/2010 |

OTHER PUBLICATIONS

Medium and Long-Term Opportunities and Risks of the Biotechnologial Production of Bulk Chemicals from Renewable Resources—The Potential of White Biotechnology—The BREW Project—Final Report—Prepared under the European Commission's GRXTH Programme (DG Research) Utrecht, Sep. 2006 (pp. 29-31).
Ullmann Encyl. Industr. Chem., $5^{th}$ Ed., vol. A6, (1988), pp. 401-477.
Polymer Science Dictionary, M.S.M., Elsevier Applied Chemistry, London and New York 1989, p. 86.
Perry's chemical Engineers' Handbook, Sixth Edition, Section 21, pp. 21-55.
E. Milchert et al., "Installation for the Recovery of Dichloropropanols and Epichlorohydrin from the Waste Water in Epichlorohydrin Production", Pol. J. Appl. Chem., vol. 41, p. 113-118 (1997).
Kielboehmer W., et al, Solvay Werk Rheinberg: Integrierte Prozesse Separierte Abwasserbehandlungen—Gewaesserschutz, Wasser, Abwasser 200 (Wissenschaftlich technische Mitteilungen des Instituts Zur Foerderung der Wasserguerte- und Wassermengenwirtschaft e; V;—2005 p. 81/-8/5., vol. 5.
Klaus Weissermel, et al., "Industrial Organic Chemistry," ($3^{rd}$ Completely Revised Edition); VCH 1997. p. 93-98.
Klaus Weissermel, et al., "Industrial Organic Chemistry," ($3^{rd}$ Completely Revised Edition); VCH 1997. p. 276-277.
Klaus Weissermel, et al., "Industrial Organic Chemistry," ($3^{rd}$ Completely Revised Edition); VCH 1997. p. 347-355.
Ying Ling Liu, "Epoxy Resins from Novel Monomers with a Bis-(9,10-dihydro-9-oxa-10-oxide-10-phosphaphenanthrene-10-yl-)Substituent," Journal of Polymer Science: Part A: Polymer Chemistry, vol. 40, 359-368 (2002).
Ylng Ling Liu, "Phosphorous-Containing Epoxy Resins from a Novel Synthesis Route," Journal of Applied Polymer Science, vol. 83, 1697-1701 (2002).
M. Schellentrager, "Untersuchungen zur oxidation Entfarbung aus gewahlter Reaktivfarbstoffe: Analyse der Abbauprodukte misteels hochauflosender LC-MS", Dissertation, XP 0002548413 (Jan. 1, 2006) w/ English Abstract.
U.S. Appl. No. 60/734,659, filed Nov. 8, 2005.
U.S. Appl. No. 60/734,627, filed Nov. 8, 2005.
U.S. Appl. No. 60/734,657, filed Nov. 8, 2005.
U.S. Appl. No. 60/734,658, filed Nov. 8, 2005.
U.S. Appl. No. 60/734,635, filed Nov. 8, 2005.
U.S. Appl. No. 60/734,634, filed Nov. 8, 2005.
U.S. Appl. No. 60/734,637, filed Nov. 8, 2005.
U.S. Appl. No. 11/915,046, filed Nov. 20, 2007, Krafft, et al.
U.S. Appl. No. 60/734,636, filed Nov. 8, 2005.
U.S. Appl. No. 11/915,088, filed Nov. 20, 2007, Krafft, et al.
U.S. Appl. No. 60/560,676, filed Apr. 8, 2004, Gilbeau, et al.
U.S. Appl. No. 61/013,680, filed Dec. 14, 2007, Krafft, et al.
U.S. Appl. No. 61/013,704, filed Dec. 14, 2007, Gilbeau, et al.
U.S. Appl. No. 61/013,676, filed Dec. 14, 2007, Borremans.
U.S. Appl. No. 61/013,707, filed Dec. 14, 2007, Krafft, et al.
U.S. Appl. No. 61/013,672, filed Dec. 14, 2007, Krafft, et al.
U.S. Appl. No. 61/013,713, filed Dec. 14, 2007, Gilbeau.
U.S. Appl. No. 61/013,710, filed Dec. 14, 2007, Krafft, et al.
U.S. Appl. No. 61/007,661, filed Dec. 14, 2007, Boulos, et al.
U.S. Appl. No. 12/529,777, filed Sep. 3, 2009, Krafft, et al.
U.S. Appl. No. 12/527,538, filed Aug. 17, 2009, Gilbeau, et.
U.S. Appl. No. 12/600,018, filed Nov. 13, 2009, Borremans.
U.S. Appl. No. 12/529,778, filed Sep. 3, 2009, Krafft, et al.
U.S. Appl. No. 12/663,749, filed Dec. 9, 2009, Krafft, et al.
U.S. Appl. No. 12/663,753, filed Dec. 9, 2009, Krafft, et al.
U.S. Appl. No. 12/663,887, filed Dec. 10, 2009, Krafft, et al.
U.S. Appl. No. 12/663,744, filed Dec. 9, 2009, Boulos, et al.
Herman A. Bruson, et al., "Thermal Decomposition of Glyceryl Carbonates," Journal of the American Chemical Society, vol. 74, Apr. 1952 pp. 2100-2101.
Perry's Chemical Engineers Handbook 7th Ed., 11th Section, 1997, pp. 11.1-11.118 (submitted into two parts).
Perry's Chemical Engineers Handbook 7th Ed., 13th Section, 1997, pp. 13.1-13.108.
Perry's Chemical Engineers Handbook 7th Ed., 15th Section, 1997, pp. 15.1-15.47.
Ullmann's Encyclopedia of Industrial Chemistry 5th Ed., vol. A23, 1993, pp. 635-636.
Ullmann's Encyclopedia of Industrial Chemistry 5th Ed., vol. A13, 1989, p. 289.
Ullmann's Encyclopedia of Industrial Chemistry 5th Ed., vol. A11, 1988, pp. 354-360.
Application No. FR 06.05325 filed Jun. 14, 2006 by Solvay S.A.—priority document to EP2007/55742 published as WO 2007/144335 (attached herein) 17 pgs.
Application No. FR 07.53863 filed Mar. 15, 2007 by Solvay S.A. and published as FR2913683, 19 pgs (attached herein)—priority document to EP2007/55742 published as WO2007/144335 29 pgs.
Gibson, "The preparation, properties, and uses of glycerol derivatives, Part III. The Chlorohydrins", 1931, Chemistry and Industry, Chemical Society, pp. 949-975.
Carre et al, 1931, "La transformation des alcools polyatomiques en mono-et en polychlorohydrines au moyen du chlorure de thionyle", Bulletin De La Societe Chimique De France, Societe Francaise De Chimie. Paris—ISSN 0037-8968, vol. 49, No. 49, pp. 1150-1154.
Fauconner, 1888, "Preparation de l'epichlorhydrine", Bull. Soc. Chim. FR, No. 50, pp. 212-214 (with enclosed translation in English).
Ullmann's Encyclopedia of Industrial Chemistry, "Industrially important epoxides", 1987, 5th Ed., vol. A9, pp. 539-540.
Bonner et al, "The composition of constant boiling hydrochloric acid at pressures of 50 to 1220 millimeters", 1930, Journal of American Chemical Society, vol. 52, pp. 633-635.
Muskof et al, "Epoxy Resins" in Ullmann's Encyclopedia of Industrial Chemistry, 1987, 5th Ed., vol. A9, pp. 547-563.
Novelli, A., "The preparation of mono-and dichlorohydrins of glycerol", 1930, Anales Farmacia Bioquimica, vol. 1, pp. 8-19 (with English abstract).
Derwent Publications, AN 109:6092 CA, JP 62-242638, Oct. 23, 1987, 1 pg.
Derwent Publications, AN 1987-338139 [48], JP 62-242638, Oct. 23, 1987, 1 pg.
I. Miyakawa et al, Nagoya Sangyo Kagaku Kenkyusho Kenkyu Hokoku, 10, 49-52 (1957). (Abstract in English only). 1 pg.
Han Xiu-Ying et al, Shanxi Daxue Xuebao Bianjibu, 2002, 25(4), 379-80. (Abstract in English only), 1 pg.
Semendyaeva et al, 1981. Khimicheskaya Promyshlennost, Seriya: Khomaya Promyshlennost, 5. 21-2 (CA Summary). XP 002465275, 1 pg.

Rudnenko, EV, et al., 1988, Lakokrasochnye Materially i 1kh Primenenie, 4 69-71 (CA Summary) XP 002465276, 1 pg.

Kirk-Othmer Encyclopedia of Chemical Technology, 1978, 3rd Ed., vol. 4, Blood, Coagulants and Anticoagulants to Cardiovascular Agents. p. 847-848.

Jeffrey Lutje Spelberg, et al, A Tandem Enzyme Reaction to Produce Optically Active Halohydrins, Epoxides and Diols, Tetrahedron: Asymmetry, Elsevler Science Publishers, vol. 10, No. 15, 1999, pp. 2863-2870.

Oleoline.com. Glycerine Market report, Sep. 10, 2003, No. 62, 31 pgs.

Notification Under Act. No. 100/2001, Coll. As Amended by Act No. 93/2004, Coll. To the extent of Annex No. 4 (SPOLEK) Nov. 30, 2004, 80 pgs.

Documentation Under Act. No. 100/2001 Coll. As Amended by Act. No. 93/2004 Coll in the scope of appendix No. 4 (SPOLEK) Jan. 11, 2005, 86 pgs.

K. Weissermel & H.J. Arpe, Industrial Organic Chemistry, Third, Completely Revised Edition, VCH, 1997, pp. 149 & 275.

Industrial Bioproducts: "Today and Tomorrow." Energetics, Inc. for the U.S. Department of Energy, Office of Energy Efficiency and Renewable Energy, Office of the Biomass Program, Jul. 2003, pp. 49, 52 to 56.

Kirk Othmer Encyclopedia of Chemical Technology, Fourth Edition, 1992, vol. 2, p. 156, John Wiley & Sons, Inc.

Ullmann's Encyclopedia of Industrial Chemistry, Fifth, Completely Revised Edition, 1988, vol. A13, pp. 292-293.

The Merck Index, Eleventh Edition, 1989, pp. 759-760.

Ullmann's Encyclopedia of Industrial Chemistry, Fifth completely Revised Edition, vol. A1, 1985, pp. 427-429.

Ullmann's Encyclopedia of Industrial Chemistry, Fifth Completely Revised Edition, vol. A6, 1986, pp. 240-252.

Hancock, E.G., Propylene and its Industrial Derivatives, 1973, pp. 298-332.

K. Weissermel & H.J. Arpe, Industrial Organic Chemistry, Third, Completely Revised Edition, VCH 1997, pp. 149-163.

K. Weissermel & H.J. Arpe, in Industrial Organic Chemistry, Third, Completely Revised Edition, VCH 1997, pp. 275-276.

Ullmann's Encyclopedia of Industrial Chemistry, Fifth Completely Revised Edition, vol. A9, 1987, pp. 539-540.

Perry's Chemical Engineers' Handbook, Sixth Edition, Robert H. Perry, Don Green, 1984, Section 21-64 to 21-68.

Iwanami et al, Dictionary of Physics and Chemistry, Third Edition, Ryo Midorikawa /Iwanami Shoten, Publishers, May 29, 1971, pp. 270-271, 595 and 726.

Expert Opinion on the Environment Impact Assessment Documentation Pursuant to Annex No. 5 of Act No. 100/2001 Coll., as amended by later regulations of the project/intent combined process for the manufacture of epichlorohydrin (SPOLEK) Apr. 2005.

Kirk Othmer Encyclopedia of Chemical Technology, Third Edition, vol. 12, 1980, pp. 1002-1005.

Chemical Engineering Handbook, the 6th Edition, Edited by the Society of Chemical Engineers, published by Maruzen Co, Ltd., 1999, pp. 1296-1306 Pub. Feb. 25, 1999 w/English translation of p. 1296, Table 28.4, p. 1298, left column, lines 4-13 and p. 1305, Table 28.10.

Product Brochure of De Dietrich Company, Apr. 1996, pp. 3, 8 and 9 w/English translation of p. 8, left column, lines 1-4, p. 9.

The Journal of the American Chemical Society, vol. XLV, Jul.-Dec. 1923, pp. 2771-2772.

Berichte Der Deutschen Chemischen Gesellschaft, 1891, vol. 24, pp. 508-510.

Catalogue of Nittetu Chemical Engineering Ltd. (Published in Mar. 1994).

12093 Chemicals, The Chemical Daily Co., Ltd. (Published on Jan. 22, 1993) with attached English translation of relevant excerpts, 24 pgs.

Chemicals Guide, Chemical Daily Co., Ltd. (Published on Jun. 15, 1990) with attached English translation of relevant excerpts.

Robert T. Morrison & Robert N. Boyd, Organic Chemistry, 5th Ed., vol. II, pp. 666 to 667 and 712 to 714 (Japanese Translation), published on Jul. 10, 1970, Tokyo Kagaku Dozin Co., Ltd. (and similar passages but retrieved from the English Fifth Edition of the Book, 1987).

J.B. Conant, et al, "Glycerol a,y-dichlorohydrin", Organic Syntheses Coll., 1941, vol. 1, p. 292-294 (5 pp.).

Gilman H., Organic Synthesis, Section 1, pp. 234-235 (no date)—attached English translation only.

Industrial Chemical Encyclopedia 5, p. 457 (no date)—attached English translation only.

"Epoxy resins", p. 36-46, by Shangai Resin Plant, Shangai People's Press, 1971—attached English translation only.

Martinetti, R. et al. "Environnement Le Recyclage du l'eau" Industrie Textile, Ste Sippe Sarl, Metz, FR, No. 1300 (Jul. 1, 1998), ISSN: 0019-9176 (no English abstract available)—8 pp.

"Rainwater Harvesting and Utilization" (United Nations Environment Program) Mar. 2002; XP003003726; Internet Citation extracted online on Jan. 1, 2006: URL:http://www.unep.or.ip/Ietc/Publication—4 pp.

Myszkowski, J. et al. "Removal of chlorinated organic impurities from hydrogen chloride"; English Chemical Abstract summary only of Polish Patent No. 136598 B2 (Mar. 31, 1986); XP002352444; 1 pp.

Myszkowski, J. et al. "Removal of organic compounds from gaseous hydrogen chloride by an absorption method" Chemia Stosowana (1986) vol. 30(4) p. 545-51; English Chemical Abstract Summary only; XP002352445; 1 pp.

Milchert, E. et al. "Recovering hydrogen chloride and organic chloro compounds from the reaction mixture in the chlorination of ethylene"; English Chemical Abstract Summary only of Polish Patent No. 162910 B1 (Jan. 31, 1994); XP002352443; 1 pp.

Laine, D.F. et al. "The destruction of organic pollutants under mild reaction conditions; A review" Michochemical Journal, vol. 85, No. 2, 2007 pp. 183-193; available online Aug. 17, 2006; 12 pp.

U.S. Appl. No. 12/681,083, filed Mar. 31, 2010, Bobet, et al.

[Unknown Author], Kirk Othmer Encyclopedia of Chemical Technology—vol. 2, p. 156, John Wiley and Sons, 1992.

U.S. Appl. No. 12/745,802, Patrick Gilbeau, et al.

RD 436093, Aug. 10, 2000, Akzo Nobel.

Ullmann's Encyclopedia of Industrial Chemistry, 2005, "pH Measurement and Control", Wiley-VCH GmbH & Co. KGaA, Weinheim, 10.1002/14356007.e19_e01; pp. 1-31 (32 pgs).

Ma Zengxin, Gan Yicui, Recovery of Polyglycerol from Residues of Synthetic Glycerol—Riyong Huaxue Gongye, 1997, 4, 21023 (Abstract Only).

U.S. Appl. No. 12/935,538, filed Sep. 29, 2010, Gibeau, et al.

Perry's Chemical Engineers Handbook, Sixth Edition, McGraw Hill Inc., (1984) Section 18.

vol. B3: Unit Operations II of Ullmann's Encyclopedia of Industrial Chemistry, Fifth Completely Revised Edition, Published by VCH, 1988.

U.S. Appl. No. 13/051,007, filed Mar. 18, 2011, Krafft, et al.

U.S. Appl. No. 13/063,230, filed Mar. 10, 2011, Krafft, et al.

Production and Prospect of the World Natural Glycerol by Zhu Shiyong, Cereals and Oils, vol. 1, 1997, pp. 33-38 (No Engiish Translation).

Vinnolit; Vinnolit receives EU grant for water recycling project; Press Release, 2008: http://www.vinnolit.de/vinnolit.nsf/id/EN_Vinnolit_receives_EU_grant_for_water_recycling_project_.

N.W. Ziels, Journal of American Oil Chemists' Society, Nov. 1956, vol. 33, pp. 556-565.

U.S. Appl. No. 13/060,421, filed Feb. 23, 2011, Balthasart, et al.

W. Giger et al., "14C/12C-Ratios in Organic Matter and Hydrocarbons Extracted from Dated Lake Sediments," Nuclear Instruments and Methods in Physics Research B5 (1984), 394-397. XP-002631954.

Jurgen O. Metzger, "Fats and Oils as Renewable Feedstock for Chemistry," Eur. J. Lipid Sci. Technol. (2009), 111, 865-876. XP-002631953.

Bruce M. Bell, "Glycerin as a Renewable Feedstock for Epichlorohydrin Production. The GTE Process," Clean-Soil, Air, Water, vol. 36, No. 8, (2008) pp. 657-661. XP-002631952.

Sang Hee Lee, et al., "Direct Preparation of Dichloropropanol (DCP) from Glycerol Using Heteropolyacid (HPA) Catalysts: A Catalyst Screen Study," Catalysis Communications (9), 2008, 1920-1923.

U.S. Appl. No. 13/131,516, filed May 26, 2011, Gilbeau, et al.

Azeotropic Data-III Compiled by Lee H. Horsley, The Dow Chemical Co., Midland, Mich., American Chemical Society (1973).

Yoshikazu Suzawa et al., Kagachu Sohchi (Chemical Apparatuses), vol. 23, No. 11, 3744, (published on Nov. 1981) with English translation.

Journal of American Oil Chemists' Society Jul. 1982, vol. 59, No. 7 pp. 292-295.

Chemical Engineering Handbook, 6th Revised Edition, 2nd print issued on Apr. 25, 2001, with attached English translation.

Organic synthesis, Part 1, published by Scientific Publishing, 1957.

Handbook of chemical products, organic chemical materials, Second edition, published by Chemical Industry Press, Jan. 1995.

R. A. Kiseleva and V.M. Goncharko, J. Appl. Chem. USSR, 1971, vol. 44, pp. 2086-2090.

Handbook of Corrosion data and material selection, published by Chemical Industry Press, edited by Jingyi Zuo, Yu Zuo; first edition, Oct. 1995 with attached English translation.

Handbook of azeotropic mixture, edited by information department of comprehensive scientific technology research institution of Fushun city, 1993.

Industry chemical reaction and application, pubished by Chinese Scientific Technology University Press, 1999 with attached English translation.

Epoxy resin, pubished by Shanghai People's Publishing House, 1971, with attached English translation.

Boschan and S. Winstein, Journal of the American Chemical Society, 1956, vol. 78, pp, 4921-4925.

Encyclopaedia for Chinese Adult Education, 1994, p623.

"Electrolytic cell test for electrolysis of epoxy sewage salt to prepare chlor-alkali", process Equipment Department of Research Institute of chlor-alkali, Shengyang chemical Plant, Liaononhg Chemical Industry, Issue n°2, pp. 32-37, published Dec. 31, 1981, with attached English translation.

"Analysis of the Composition of the Byproduct During the Manufacturing Process of Sepichlorhydrin by GC-MS", Ren Chengxin et al., Chemical Analysis and Measurement, vol. 12, Issue n°3, p. 25-26, Dec. 31, 2003, with attached English translation.

Encyclopedia of Chemical Technology, vol. 5, Nov. 1993.

Manufacture and use of epoxy resin, edited by Shanghai Resin Factory, published by China Petrochemical Press, First Edition, Oct. 1974.

* cited by examiner

CRUDE GLYCEROL-BASED PRODUCT, PROCESS FOR ITS PURIFICATION AND ITS USE IN THE MANUFACTURE OF DICHLOROPROPANOL

The present application is a U.S. national stage application under 35 U.S.C. §371 of International Application No. PCT/EP2007/055742, filed Jun. 12, 2007, which claims benefit of French patent applications FR 06/05325 and FR 07/53863 filed respectively on Jun. 14, 2006 and Mar. 15, 2007, the contents of all of these applications being incorporated herein by reference.

The present invention relates to a crude glycerol-based product, to a process for its purification and to the use of the purified product in the manufacture of dichloropropanol.

Dichloropropanol, for example, is a reaction intermediate in the manufacture of epichlorohydrin and epoxy resins (Kirk-Othmer Encyclopedia of Chemical Technology, Fourth Edition, 1992, Vol. 2, page 156, John Wiley & Sons Inc.).

According to known processes, dichloropropanol can be obtained in particular by hypochlorination of allyl chloride, by chlorination of allyl alcohol and by hydrochlorination of glycerol. The latter process exhibits the advantage that the dichloropropanol can be obtained starting from fossil starting materials or renewable starting materials and it is known that petrochemical natural resources, from which the fossil materials originate, for example oil, natural gas or coal, available on the earth are limited.

It has been found that when glycerol is contaminated by various compounds, such as glycerol alkyl ethers, which can interfere with the operations for the separation and treatments of the effluents from the processes employing glycerol, it can nevertheless be used as starting material in the manufacture of dichloropropanol.

The invention consequently relates to a crude glycerol-based product comprising glycerol alkyl ethers in an amount of 0.001 to 100 g/kg of crude product.

The crude glycerol-based product generally contains at least 200 g of glycerol per kg of crude product, preferably at least 500 g of glycerol per kg of crude product, more preferably at least 750 g/kg, still more preferably at least 900 g/kg, yet more preferably at least 950 g/kg and most preferably at least 990 g/kg.

The amount of glycerol alkyl ethers is often at most 90 g/kg, commonly at most 50 g/kg, frequently at most 10 g/kg, commonly at most 5 g/kg, usually at most 1 g/kg, commonly at most 0.5 g/kg and frequently at most 0.2 g/kg. This amount is often at least 0.005 g/kg, frequently at least 0.01 g/kg, commonly at least 0.04 g/kg and usually at least 0.1 g/kg.

The glycerol alkyl ethers can be glycerol mono-, di- and/or triethers, the alkyl groups of which are selected independently from alkyl radicals comprising at least one 1 carbon atom and at most 8 carbon atoms.

These alkyl groups are preferably linear or branched or alicyclic aliphatic alkyl groups and more preferably linear or branched aliphatic groups. The ether functional group on the alkyl group is made via a primary, secondary or tertiary carbon atom. The alkyl groups are preferably selected from the methyl, ethyl, propyl, butyl, pentyl, hexyl, heptyl and octyl groups and more preferably from the methyl, ethyl, propyl and butyl groups and particularly preferably from the methyl and ethyl groups. Very particularly preferably, the alkyl group is a methyl group. The propyl group can be chosen from the n-propyl and isopropyl groups and is preferably an isopropyl group. The butyl group can be chosen from the 1-butyl, 2-butyl, isobutyl and tert-butyl groups, preferably from the isobutyl and tert-butyl groups.

The glycerol alkyl ethers can be glycerol mono-, di- and trialkyl ethers, preferably mono- and diethers and more preferably monoethers. Glycerol monomethyl, monoethyl, monopropyl, monobutyl, monopentyl, monohexyl, monoheptyl and monooctyl ethers are preferred. The monomethyl, monoethyl, monopropyl and monobutyl ethers are more preferred. The monomethyl and monoethyl ethers are more preferred still and glycerol monomethyl ethers are very particularly preferred.

The monopropyl ethers can be chosen from the n-propyl, the isopropyl ethers or mixtures thereof and are preferably isopropyl ethers. The monobutyl ethers can be chosen from the 1-butyl, 2-butyl, isobutyl, tert-butyl ethers and any mixtures of at least two of them, and are preferably chosen from isobutyl or tert-butyl ethers.

When the glycerol alkyl ethers are di- and triethers, the alkyl groups can be identical or different. These groups are preferably identical.

The preferred monoethers are 3-alkoxy-1,2-propanediol and 2-alkoxy-1,3-propanediol. The content of 3-alkoxy-1,2-propanediol in the mixture of 3-alkoxy-1,2-propanediol and of 2-alkoxy-1,3-propanediol is generally at least 50%, preferably at least 60% and very preferably at least 70%. This content is at most 95% and preferably at most 90%.

The glycerol monomethyl ethers are 3-methoxy-1,2-propanediol and 2-methoxy-1,3-propanediol. The content of 3-methoxy-1,2-propanediol in the mixture of 3-methoxy-1,2-propanediol and of 2-methoxy-1,3-propanediol is generally at least 50%, preferably at least 60% and very preferably at least 70%. This content is at most 95% and preferably at most 90%.

The glycerol monoethyl ethers are 3-ethoxy-1,2-propanediol and 2-ethoxy-1,3-propanediol. The content of 3-ethoxy-1,2-propanediol in the mixture of 3-ethoxy-1,2-propanediol and of 2-ethoxy-1,3-propanediol is generally at least 50%, preferably at least 60% and very preferably at least 70%. This content is at most 95% and preferably at most 90%.

The glycerol monopropyl ethers are 3-propoxy-1,2-propanediol and 2-propoxy-1,3-propanediol. The content of 3-propoxy-1,2-propanediol in the mixture of 3-propoxy-1,2-propanediol and of 2-propoxy-1,3-propanediol is generally at least 50%, preferably at least 60% and very preferably at least 70%. This content is at most 95% and preferably at most 90%. The propoxy group can be an n-propoxy or isopropoxy, preferably an isopropoxy group.

The glycerol monobutyl ethers are 3-butoxy-1,2-propanediol and 2-butoxy-1,3-propanediol. The content of 3-butoxy-1,2-propanediol in the mixture of 3-butoxy-1,2-propanediol and of 2-butoxy-1,3-propanediol is generally at least 50%, preferably at least 60% and very preferably at least 70%. This content is at most 95% and preferably at most 90%. The butoxy group can be chosen from the 1-butoxy, 2-butoxy, isobutoxy and tert-butoxy groups, preferably from the isobutoxy and tert-butoxy groups.

The crude glycerol-based product can also comprise alcohols. These alcohols are preferably methanol, ethanol, propanol, preferably n-propanol and/or isopropanol, butanol, preferably 1-butanol and/or 2-butanol and/or isobutanol and/or tert-butanol, pentanol, preferably 1-pentanol and/or 2-pentanol and/or 3-methyl-1-butanol, hexanol, heptanol, octanol, ethylene glycol and propylene glycol.

The crude glycerol-based product can present one or more of the following features:
the glycerol alkyl ethers are methyl ethers
it comprises methanol in an amount of 0.1 to 20 g/kg of crude product it comprises ethanol, propanol, butanol, pentanol, hexanol, heptanol, octanol, ethylene glycol and propylene glycol in a total amount of 0.01 to 2 g/kg of crude product the glycerol alkyl ethers are ethyl ethers it comprises ethanol in an amount of 0.1 to 20 g/kg of crude product it comprises methanol, propanol, butanol, pentanol, hexanol, heptanol, octanol, ethylene glycol and propylene glycol in a total amount of 0.01 to 2 g/kg of crude product the glycerol alkyl ethers are propyl ethers it comprises propanol in an amount of 0.1 to 20 g/kg of crude product it comprises methanol, ethanol, butanol, pentanol, hexanol, heptanol, octanol, ethylene glycol and propylene glycol in a total amount of 0.01 to 2 g/kg of crude product the glycerol alkyl ethers are butyl ethers it comprises butanol in an amount of 0.1 to 20 g/kg of crude product it comprises methanol, ethanol, propanol, pentanol, hexanol, heptanol, octanol, ethylene glycol and propylene glycol in a total amount of 0.01 to 2 g/kg of crude product.

When the glycerol alkyl ethers are methyl ethers, the methanol can be present in an amount of 0.1 to 20 g/kg of crude product and the ethanol, the propanol, the butanol, the pentanol, the hexanol, the heptanol, the octanol, the ethylene glycol and the propylene glycol can be present in a total amount of 0.01 to 2 g/kg of crude product.

When the glycerol alkyl ethers are ethyl ethers, the ethanol can be present in an amount of 0.1 to 20 g/kg of crude product and the methanol, the propanol, the butanol, the pentanol, the hexanol, the heptanol, the octanol, the ethylene glycol and the propylene glycol can be present in a total amount of 0.01 to 2 g/kg of crude product.

When the glycerol alkyl ethers are propyl ethers, the propanol can be present in an amount of 0.1 to 20 g/kg of crude product and the methanol, the ethanol, the butanol, the pentanol, the hexanol, the heptanol, the octanol, the ethylene glycol and the propylene glycol can be present in a total amount of 0.01 to 2 g/kg of crude product.

The propanol can be chosen from n-propanol, isopropanol and mixtures thereof and is preferably isopropanol.

When the glycerol alkyl ethers are butyl ethers, the butanol can be present in an amount of 0.1 to 20 g/kg of crude product and the methanol, the ethanol, the propanol, the pentanol, the hexanol, the heptanol, the octanol, the ethylene glycol and propylene glycol can be present in a total amount of 0.01 to 2 g/kg of crude product.

The butanol cane be chosen from 1-butanol, 2-butanol, isobutanol, tert-butanol and any mixtures of at least two of them, preferably from isobutanol and tert-butanol.

The crude glycerol-based product can also comprise water in an amount of at least 0.1 g/kg and of at most 100 g/kg. This amount is preferably at most 50 g/kg and more preferably at most 20 g/kg.

The crude glycerol-based product can also comprise alkyl esters of fatty acids, glycerol esters, such as, for example, mono- and diglycerides, glycerol oligomers and salts. The latter impurities may form a separate phase. The term "alkyl esters of fatty acids" is intended to denote esters of fatty acids with mono- or polyalcohols, with the exception of glycerol, the alkyl group of the ester being one of the groups described above for the glycerol alkyl ethers. These alkyl esters are preferably methyl, ethyl, propyl and butyl esters of fatty acids, more preferably methyl and ethyl esters and very particularly preferably methyl esters of fatty acids.

The content of the esters is generally of at least 0.1 g/kg, often of at least 1 g/kg and frequently of at least 5 g/kg. That content is generally of at most 50 g/kg, often of at most 30 g/kg and frequently of at most 10 g/kg.

The content of the glycerol oligomers is generally of at least 0.1 g/kg, often of at least 1 g/kg and frequently of at least 2 g/kg. That content is generally of at most 20 g/kg, often of at most 10 g/kg and frequently of at most 5 g/kg.

The content of the salts is generally of at least 0.0005 g/kg, often of at least 0.001 g/kg and frequently of at least 0.01 g/kg. That content is generally of at most 10 g/kg, often of at most 1 g/kg and frequently of at most 0.1 g/kg.

Without wishing to be committed to any theoretical explanation, it is believed that the glycerol alkyl ethers and the alcohols may originate from the process for the manufacture of glycerol, in particular by conversion of animal or vegetable fats or oils, by transesterification in the presence of an alcohol, and the process being operated under conditions such that ethers of glycerol have been formed and have not been separated from glycerol.

The invention therefore also relates to a process for manufacturing a crude glycerol-based product in which a vegetable fat or oil is reacted with an alcohol under such conditions that ethers of glycerol are formed and are not separated from glycerol.

Such conditions are for example, the use of an acidic heterogeneous catalyst, the presence of acidic compounds, for instance carboxylic acids in the fats or oils, a high transesterification temperature and a long residence time of the alcohol/vegetable fat or oil mixture on the catalyst.

The alcohol is preferably chosen from methanol, ethanol, propanol, butanol, pentanol, hexanol, heptanol, octanol and the mixtures of at least two of them, more preferably chosen from methanol, ethanol, propanol, butanol, more preferably still from methanol and ethanol. The alcohol is very particularly preferably methanol.

The propanol can be chosen from n-propanol, isopropanol and their mixtures and is preferably isopropanol. The butanol can be chosen from 1-butanol, 2-butanol, isobutanol, tert-butanol and the mixtures of at least two of them, preferably from isobutanol, tert-butanol and their mixtures.

The invention also relates to a process for the purification of the crude glycerol-based product in which the crude product is subjected to at least one treatment, optionally under reduced pressure, of evaporative concentration, of evaporative crystallization, of distillation, of fractional distillation, of stripping or of liquid-liquid extraction.

The term "evaporative concentration" is intended to denote a process of partial evaporation of the crude product which makes it possible to concentrate the residual product in less volatiles entities. The term "evaporative crystallization" is intended to denote a process resulting in the crystallization of a compound by removing, by evaporation, a compound which promotes its dissolution in the medium. These processes are described in "Perry's Chemical Engineers' Handbook" in the 11th section of the 7th edition, 1997.

The term "distillation" is intended to denote the type of separation conventional in chemical engineering and described, for example, in "Perry's Chemical Engineers' Handbook" in the 13th section of the 7th edition, 1997.

The term "fractional distillation" is understood to mean a sequence of distillations where the distillate is withdrawn batchwise.

The term "stripping" is intended to denote the separation of a substance by the entrainment by means of the vapour of a pure material. In the process according to the invention, this material can be any compound which is inert with respect to glycerol, such as, for example, steam, air, nitrogen and carbon dioxide.

The term "liquid/liquid extraction" is understood to mean bringing the crude glycerol-based product into contact with an appropriate completely or partially immiscible solvent which makes it possible to selectively extract the desired compounds, optionally according to a countercurrent process, such as are described in "Perry's Chemical Engineers' Handbook" in the 15th section of the 7th edition, 1997.

The stripping, evaporative concentration, evaporative crystallization, liquid/liquid extraction and distillation treatments can be combined, for example in a stripping column surmounted by a distillation section or in a partial evaporator feeding a distillation column or by combining a liquid/liquid extraction by a solvent, a stripping of the residual solvent present in the stream enriched in glycerol and a distillation of the solvent enriched in extracted compounds.

The glycerol alkyl ethers and the alcohols are recovered in the distilled or stripped fraction and the purified glycerol-based product constitutes the residue from the distillation or stripping treatment.

The glycerol alkyl ethers and the alcohols are generally recovered in the solvent used for the liquid/liquid extraction and the purified glycerol-based product generally constitutes the residue from the liquid/liquid extraction.

When the treatment consists of an at least partial evaporation of the crude product, the temperature of the glycerol-rich region is generally at least 0° C., often at least 80° C. and frequently at least 100° C. This temperature is generally at most 280° C., often at most 250° C., and frequently at most 200° C. The temperature in the glycerol-depleted regions is generally at least −20° C., preferably at least −10° C. and particularly preferably at least 0° C. This temperature is generally at most equal to the temperature of the glycerol-enriched region, preferably lower by at least 5° C. at this temperature, particularly preferably lower by at least 10° C. at this temperature.

When the treatment is carried out by liquid/liquid extraction, the temperature is generally greater than or equal to 20° C., preferably greater than or equal to 40° C., more particularly greater than or equal to 50° C. This temperature is generally less than or equal to 200° C., preferably less than or equal to 150° C. and more particularly preferably less than or equal to 120° C.

The pressure in the treatment is generally at least 0.001 mbar absolute. This pressure is generally at most 1 bar, often at most 0.5 bar, frequently at most 0.3 bar and more specifically at most 0.25 bar. When the treatment comprises a separated evaporation stage, the latter is generally carried out at a pressure of less than 2 bar absolute, preferably at a pressure of less than 1 bar absolute, particularly preferably at a pressure of less than 0.5 bar absolute. It is generally carried out at a pressure of at least 0.1 mbar, preferably at a pressure of at least 0.2 mbar. When the evaporation stage is combined with a distillation or fractional distillation stage, it is carried out at a pressure at least equal to the pressure of the stage carried out at the lower pressure, preferably at a pressure greater by at least 10 mbar than the pressure of the stage carried out at the lower pressure. The stripping stage is generally carried out at a pressure of less than 5 bar absolute, preferably of less than or equal to 2 bar.

In the distillation treatments, with or without stripping, the reflux ratio is generally at least 1%, often at least 5% and frequently at least 10%. This reflux ratio is at most 99% and often at most 50%. The term "reflux ratio", for a continuous distillation, is understood to mean the ration of the throughput of the vaporized fraction to the reboiler by the throughput of the residue.

The term "reflux ratio" for a fractional distillation, under batch conditions, is understood to mean the ratio of the amount vaporized with respect to the final residue.

The proportion of the distilled fraction is generally at most 150 g/kg, often at most 100 g/kg, of the crude glycerol-based product.

The evaporative concentration, evaporative crystallization, distillation, fractional distillation, stripping or liquid-liquid extraction, can be preceded or followed by an operation of separation of the possible separate phase mentioned above. This separation can, for example, be a separation by settling, a centrifuging, a filtration, an adsorption or an exchange of ions. When it is a separation by settling, the operation can be improved by passing through a coalescer. The adsorption operation is preferably an operation with adsorption on active charcoal.

After the treatment, a purified glycerol-based product is obtained comprising glycerol alkyl ethers in an amount generally of less than or equal to 5 g/kg of purified product and methanol, ethanol, propanol, butanol, pentanol, hexanol, heptanol, octanol, ethylene glycol and propylene glycol in a total amount generally of less than 1 g/kg of purified product.

The amount of glycerol alkyl ethers is preferably at most 1.0 g/kg, more preferably at most 0.5 g/kg of purified product, yet more preferably at most 0.2 g/kg, yet more preferably at most 0.1 g/kg, and still preferably at most 0.04 g/kg. This amount is more particularly preferably at most 0.01 g/kg and very particularly preferably at most 0.001 g/kg. This amount is generally at least 0.01 mg/kg.

When the glycerol alkyl ethers are methyl ethers, the amount of glycerol methyl ethers after the treatment is preferably at most 1.0 g/kg, more preferably at most 0.5 g/kg of purified product, yet more preferably at most 0.2 g/kg, yet more preferably at most 0.1 g/kg, and still preferably at most 0.04 g/kg. This amount is more particularly preferably at most 0.01 g/kg and very particularly preferably at most 0.001 g/kg. This amount is generally at least 0.01 mg/kg.

When the glycerol alkyl ethers are ethyl ethers, the amount of glycerol ethyl ethers after the treatment is preferably at most 1.0 g/kg, more preferably at most 0.5 g/kg of purified product, yet more preferably at most 0.2 g/kg, yet more preferably at most 0.1 g/kg, and most preferably at most 0.04 g/kg. This amount is more particularly preferably at most 0.01 g/kg and very particularly preferably at most 0.001 g/kg. This amount is generally at least 0.01 mg/kg.

When the glycerol alkyl ethers are propyl ethers, the amount of glycerol propyl ethers after the treatment is preferably at most 1.0 g/kg, more preferably at most 0.5 g/kg of purified product, yet more preferably at most 0.2 g/kg, yet more preferably at most 0.1 g/kg, and most preferably at most 0.04 g/kg. This amount is more particularly preferably at most 0.01 g/kg and very particularly preferably at most 0.001 g/kg. This amount is generally at least 0.01 mg/kg.

The propyl ethers can be chosen from n-propyl ether, isopropyl ether and mixtures thereof, and are preferably isopropyl ethers.

When the glycerol alkyl ethers are butyl ethers, the amount of glycerol butyl ethers after the treatment is preferably at most 1.0 g/kg, more preferably at most 0.5 g/kg of purified product, yet more preferably at most 0.2 g/kg, yet more preferably at most 0.1 g/kg, and most preferably at most 0.04 g/kg. This amount is more particularly preferably at most 0.01 g/kg and very particularly preferably at most 0.001 g/kg. This amount is generally at least 0.01 mg/kg.

The butyl ethers can be chosen form 1-butyl ether, 2-butyl ether, isobutyl ether, tertbutyl ether and any mixtures of at least two of them, preferably from isobutyl and tert-butyl ethers.

The amount of methanol, ethanol, propanol, butanol, pentanol, hexanol, heptanol, octanol, ethylene glycol and propylene glycol after the treatment is preferably at most 0.1 g/kg of purified product, more preferably at most 0.01 g/kg and very particularly preferably at most 0.001 g/kg.

When the glycerol alkyl ethers are methyl ethers, the total amount of methanol, ethanol, propanol, butanol, pentanol, hexanol, heptanol, octanol, ethylene glycol and propylene glycol after the treatment is preferably at most 0.1 g/kg of purified product, more preferably at most 0.01 g/kg and very particularly preferably at most 0.001 g/kg.

When the glycerol alkyl ethers are ethyl ethers, the total amount of methanol, ethanol, propanol, butanol, pentanol, hexanol, heptanol, octanol, ethylene glycol and propylene glycol after the treatment is preferably at most 0.1 g/kg of purified product, more preferably at most 0.01 g/kg and very particularly preferably at most 0.001 g/kg.

When the glycerol alkyl ethers are propyl ethers, the total amount of methanol, ethanol, propanol, butanol, pentanol, hexanol, heptanol, octanol, ethylene glycol and propylene glycol after the treatment is preferably at most 0.1 g/kg of purified product, more preferably at most 0.01 g/kg and very particularly preferably at most 0.001 g/kg.

When the glycerol alkyl ethers are butyl ethers, the total amount of methanol, ethanol, propanol, butanol, pentanol, hexanol, heptanol, octanol, ethylene glycol and propylene glycol after the treatment is preferably at most 0.1 g/kg of purified product, more preferably at most 0.01 g/kg and very particularly preferably at most 0.001 g/kg.

The propanol can be chosen from n-propanol, isopropanol and mixtures thereof, and is preferably isopropanol. The butanol can be chosen from 1-butanol, 2-butanol, isobutanol, tert-butanol and any mixture of at least two of them, and is preferably isobutanol or tert-butanol.

The treatment also makes it possible to reduce the content of water and of alkyl esters of the crude glycerol-based product.

The content of water in the purified glycerol-based product is generally of at least 0.01 g/kg, often of at least 0.1 g/kg and frequently of at least 0.5 g/kg. That content is generally of at most 10 g/kg, often of at most 5 g/kg and frequently of at most 1 g/kg.

The content of the esters in the purified glycerol-based product is generally of at least 0.01 g/kg, often of at least 0.1 g/kg and frequently of at least 0.5 g/kg. That content is generally of at most 10 g/kg, often of at most 5 g/kg and frequently of at most 1 g/kg.

The invention also relates to a purified glycerol-based product comprising glycerol alkyl ethers in an amount of 0.01 mg/kg to 1 g/kg of purified product, preferably of 10 mg/kg to 500 mg/kg of purified product and more preferably of 40 mg/kg to 200 mg/kg of purified product.

The purified glycerol-based product can be obtained by subjecting the crude glycerol-based product of the invention to at least one treatment, optionally under reduced pressure, of evaporative concentration, of evaporative crystallization, of distillation, of fractional distillation, of stripping or of liquid-liquid extraction, as described above.

The invention also relates to a process for the manufacture of dichloropropanol starting from glycerol in which a crude glycerol-based product is subjected to at least one treatment, optionally under reduced pressure, of evaporative concentration, of evaporative crystallization, of distillation, of fractional distillation, of stripping or of liquid-liquid extraction so as to reduce the content of the glycerol alkyl ethers and to obtain a purified glycerol-based product which is reacted with a chlorinating agent.

The glycerol alkyl ethers are preferably methyl ethers or ethyl ethers, more preferably methyl ethers.

The invention also relates to a process for the manufacture of epichlorohydrin, comprising the process for the manufacture of dichloropropanol in which the purified glycerol-based product is reacted with a chlorinating agent, followed by a process for the dehydrochlorination of dichloropropanol The crude glycerol-based product in the process for manufacturing dichloropropanol according to the invention may be obtained starting from fossil raw materials or starting from renewable raw materials, preferably starting from renewable raw materials, as described in WO 2005/054167 of SOLVAY SA, the content of which is incorporated herein by reference, and especially the passages from page 1, line 26, to page 4, line 2, and as described in WO 2006/100312 of SOLVAY SA, the content of which is incorporated herein by reference, and especially the passages from page 3, line 29, to page 5, line 24.

In the process for preparing dichloropropanol according to the invention, glycerol may have an alkali metal and/or alkaline earth metal content as described in WO 2006/100315 of SOLVAY SA, the content of which is incorporated herein by reference, and especially the passages from page 7, line 11, to page 9, line 10.

In the process for preparing dichloropropanol according to the invention, the glycerol may contain elements other than alkali metals and alkaline earth metals as described in WO 2006/100319 of SOLVAY SA, the content of which is incorporated herein by reference, especially the passages from page 2, line 3 to 8, and from page 6, line 20, to page 9, line 14.

In the process for preparing dichloropropanol according to the invention, the glycerol contains generally an amount of heavy compounds other glycerol and whose boiling temperature under a pressure of 1 bar absolute is at least 15° C. greater than the boiling temperature of dichloropropanol as described in WO 2006/1000319 of SOLVAY SA the content of which is incorporated herein by reference, especially the passages from page 9, line 15, to page 10, line 15.

In the process for preparing dichloropropanol according to the invention, the chlorinating agent generally comprises hydrogen chloride. The hydrogen chloride can be gaseous hydrogen chloride, optionally anhydrous, an aqueous hydrogen chloride solution or a mixture of the two.

The chlorinating agent can originate at least partially from a process for the manufacture of vinyl chloride and/or of 4,4-methylenediphenyl diisocyanate and/or for the pyrolysis of chlorinated organic compounds and/or for the pickling of metals and/or for the production of dichloropropanol by hypochlorination of allyl chloride and/or be generated in situ in the reaction medium starting from an inorganic acid and from a metal chloride, such as described in Application WO 2005/054167 on behalf of SOLVAY SA, the content of which is incorporated herein by reference, especially the passages from page 4, line 32, to page 5, line 18.

The chlorinating agent can originate at least partially from a process for the manufacture of allyl chloride and/or from a process for the manufacture of chloromethanes and/or from a chlorinolysis process and/or from a process for the oxidation of chlorinated compounds at a temperature of greater than or equal to 800° C., such as described in Application WO 2006/106153 on behalf of SOLVAY SA, the content of which is incorporated herein by reference, especially the passages from page 2, line 10, to page 3, line 20.

The chlorinating agent can also originate at least partially from a process for the manufacture of silica by decomposition of chlorosilane, such as described in Ullmann's Encyclopedia of Industrial Chemistry, Fifth Completely Revised Edition, Volume A 23: Refractory Ceramics to Silicon Carbide, 1993, pages 635-636. The hydrogen chloride is provided in this case generally in the form of an aqueous hydrogen chloride solution.

The chlorinating agent can also originate at least partially from a process for the manufacture of hydrogen chloride by direct synthesis starting from chlorine and hydrogen, such as described in Ullmann's Encyclopedia of Industrial Chemistry, Fifth Completely Revised Edition, Volume A 13: High-Performance Fibers to Imidazole and Derivatives, 1989, page 289. The hydrogen chloride is provided in this case generally in the form of a gas or of a liquefied gas or of an aqueous solution. In this process for the manufacture of hydrogen chloride, the chlorine and hydrogen can originate from any process. The chlorine and hydrogen preferably originate at least partially from a process for the electrolysis of a brine, more preferably of a brine predominantly comprising sodium chloride, potassium chloride or a mixture of the two and particularly preferably of a brine predominantly comprising sodium chloride. The electrolysis process can be a mercury, diaphragm or membrane electrolysis process.

The chlorinating agent can also originate at least partially from a chlorine/fluorine exchange process on organic compounds, such as processes for the manufacture of chlorofluorohydrocarbons (HCFCs) and/or of hydrofluorocarbons (HFCs). This chlorinating agent can be in the gas form or in the form of an aqueous solution. A description of processes for the manufacture of H(C)FCs can be found in the reference work Ullmann's Encyclopedia of Industrial Chemistry, Fifth Completely Revised Edition, Volume A 11: Fibers, 5. Synthetic Inorganic, to Formaldehyde, 1988, pages 354-360. Preference is given among these processes to the processes for the manufacture of HFC-134a, HFC-152a, CFC-11, CFC-12, HFC-32, HCFC-142b, HCFC-141b and HFC-143a. The hydrogen chloride resulting from these processes generally exhibits a content of hydrogen fluoride in the hydrogen chloride of less than or equal to 200 mg/kg, preferably of less than or equal to 50 mg/kg and very preferably of less than or equal to 10 mg/kg. Without wishing to be restricted by any one theoretical explanation, it is believed that an excessively high content of hydrogen fluoride in the hydrogen chloride used as starting material would result in the rapid corrosion of the materials generally used in the equipment for the production of dichloropropanol from glycerol, such as the enamel of the enamelled steel, for example.

The invention also relates to a process for the manufacture of dichloropropanol from glycerol, according to which glycerol obtained by the process for the purification of the crude glycerol-based product described above is subjected to a reaction with a chlorinating agent comprising hydrogen chloride which was obtained at least partially in a process for the manufacture of silica by decomposition of chlorosilane and/or in a process for the manufacture of hydrogen chloride by direct synthesis starting from chlorine and hydrogen and/or in a chlorine/fluorine exchange process on organic compounds.

The invention also relates to a process for the manufacture of dichloropropanol according to which glycerol is subjected to a reaction with a chlorinating agent comprising hydrogen chloride which was obtained at least partially in a process for the manufacture of silica by decomposition of chlorosilane and/or in a process for the manufacture of hydrogen chloride by direct synthesis starting from chlorine and hydrogen and/or in a chlorine/fluorine exchange process on organic compounds.

The invention also relates to a chlorinating agent comprising hydrogen chloride and at most 200 mg/kg of hydrogen fluoride per kg of hydrogen chloride.

This chlorinating agent can be obtained in a chlorine/fluorine exchange process on organic compounds, such as processes for the manufacture of chlorofluorohydrocarbons (HCFCs) and/or of hydrofluorocarbons (HFCs).

In the process for preparing dichloropropanol according to the invention, the reaction of glycerol with the chlorinating agent may be carried out in a reactor as described in application WO 2005/054167 of SOLVAY SA, the content of which is herein incorporated by reference, especially the passages from page 6, line 3 to line 23.

In the process for preparing dichloropropanol according to the invention, the reaction of glycerol with the chlorinating agent may be carried out in apparatus which is made of or covered with materials that are resistant to chlorinating agents, as described in the patent WO 2006/100317 of SOLVAY SA, the content of which is incorporated here by reference, especially the passages from page 2, line 29, to page 3, line 7, and from page 23, line 22, to page 27, line 25.

In the process for preparing dichloropropanol according to the invention, the reaction of glycerol with the chlorinating agent may be carried out in a reaction medium as described in WO 2006/106154 of SOLVAY SA, the content of which is incorporated here by reference, especially the passages from page 14, line 15, to page 17, line 10.

In the process for preparing dichloropropanol according to the invention, the reaction of glycerol and the chlorinating agent may be carried out in the presence of a catalyst as described in WO 2005/054167 of SOLVAY SA, the content of which is incorporated here by reference, especially the passages from page 6, line 24, to page 7, line 35.

Mention is made particularly of a catalyst based on a carboxylic acid or on a carboxylic acid derivative having an atmospheric boiling point of greater than or equal to 200° C., especially adipic acid and derivatives of adipic acid.

In the process for preparing dichloropropanol according to the invention, the reaction of glycerol and the chlorinating agent may be carried out at a catalyst concentration, temperature and pressure and for residence times as described in WO 2005/054167 of SOLVAY SA the content of which is incorporated here by reference, especially the passages from page 8, line 1, to page 10, line 10.

Mention is made particularly of a temperature of at least 20° C. and not more than 160° C., of a pressure of at least 0.3 bar and not more than 100 bar and of a residence time of at least 1 h and not more than 50 h.

In the process for the manufacture of dichloropropanol according to the invention, the reaction of glycerol and the chlorinating agent may be carried out as described in WO2007/054505 of SOLVAY SA, the content of which is incorporated herein by reference, especially the passages from page 1, line 24 to 31, and from page 2, line 24, to page 6, line 18. Glycerol is preferably reacted with a chlorinating agent comprising hydrochloric acid in a liquid medium in equilibrium with a vapour phase and in which the condensation of a fraction exhibiting the composition of the vapour phase is prevented. In the process, the liquid medium is in a vessel, and is in equilibrium with a vapour phase and at least one part of the inner wall of the vessel which is above the level of the liquid medium in the vessel is maintained at a temperature lower than 120° C. or at a temperature at least 1° C. higher than the dew temperature of the vapour phase and/or is trickled with a liquid.

The chlorination reaction can be carried out in the presence of a solvent.

In the process for preparing dichloropropanol according to the invention, the reaction of glycerol with the chlorinating agent may be carried out in the presence of a solvent as described in WO 2005/054167 of SOLVAY SA, the content of which is incorporated here by reference, especially the passages from page 11, line 12 to line 36.

In the process for preparing dichloropropanol according to the invention, the reaction of glycerol with the chlorinating agent may be carried out in the presence of a liquid phase comprising heavy compounds other than glycerol, as described in the WO 2006/100316 of SOLVAY SA, the content of which is incorporated here by reference, especially the passages from page 2, line 18 to 20, and from page 15, line 32, to page 17, line 33.

The chlorination reaction is preferably carried out in a liquid reaction medium, as described in the WO 2006/100319 of SOLVAY SA, the content of which is incorporated here by reference, especially the passages from page 2, line 3 to 8, and from page 17, line 12, to page 19, line 9.

In the process according to the invention, the separation of the dichloropropanol and of the other compounds from the reaction mixture may be carried out in accordance with the methods as described in WO 2005/054167 of SOLVAY SA, the content of which is incorporated herein by reference, especially the passages from page 12, line 1, to page 17, line 20.

Particular mention is made of separation by azeotropic distillation of a water/dichloropropanol/chlorinating agent mixture under conditions which minimize the losses of chlorinating agent, followed by isolation of the dichloropropanol by decantation.

In the process for preparing dichloropropanol according to the invention, the isolation of the dichloropropanol and of the other compounds from the reaction mixture from chlorination of glycerol may be carried out in accordance with methods of the kind described in WO 2006/100312 of SOLVAY SA, the content of which is incorporated here by reference, especially the passages, from page 2, line 3 to 10, from page 20, line 28, to page 25, line 2, and from page 25, line 21, to page 28, line 20.

In the process for preparing dichloropropanol according to the invention, the separation of the dichloropropanol and of the other compounds from the reaction mixture from chlorination of glycerol may be carried out in accordance with methods as described in WO 2006/100313 of SOLVAY SA, the content of which is incorporated here by reference, especially the passages from page 2, line 1 to line 13, and from page 21, line 13, to page 25, line 25.

In the process for preparing dichloropropanol according to the invention, the separation of the dichloropropanol and the other compounds from the reaction mixture from chlorination of glycerol may be carried out in accordance with methods as described in WO 2006/100314 of SOLVAY SA, the content of which is incorporated herein by reference, especially the passages from page 2, line 6 to 31, and from page 18, line 33, to page 22, line 29.

In the process for preparing dichloropropanol according to the invention, the separation of the dichloropropanol and of the other compounds from the reaction mixture from chlorination glycerol, may be carried out in accordance with methods as described in WO 2006/100320 of SOLVAY SA, the content of which is incorporated herein by reference, especially the passages from page 1, line 30, to page 2, line 12, and from page 6, line 25, to page 10, line 28.

In the process for preparing dichloropropanol according to the invention, the isolation and the treatment of the other compounds of the reaction mixture from chlorination of glycerol may be carried out in accordance with methods as described in WO 2006/100315 of SOLVAY SA, the content of which is incorporated herein by reference, especially the passages from page 2, line 3 to line 13, and from page 23, line 3, to page 24, line 13. A preferred treatment consists in subjecting a fraction of the by-products of the reaction to a high-temperature oxidation.

In the process for preparing dichloropropanol according to the invention, the dichloropropanol is generally obtained in the form of a mixture of compounds comprising the isomers of 1,3-dichloropropan-2-ol and 2, 3-dichloropropan-1-ol, as described in WO 2006/100319 of SOLVAY SA, the content of which is incorporated herein by reference, especially the passages from page 23, line 34, to page 24, line 25.

In the process for preparing dichloropropanol according to the invention, the dichloropropanol may include a heightened amount of halogenated ketones, in particular of chloroacetone, as described in WO 2006/100311 of SOLVAY SA, the content of which is incorporated herein by reference, especially the passages from page 2, line 22 to 25, from page 22, line 8, to page 23, line 35.

The dichloropropanol formed can be separated from the other constituents of the reaction medium by any separation treatment, for example by distillation, stripping, extraction or adsorption. After this treatment, the other constituents of the reaction medium can be subjected to additional separation treatments, such as, for example, a filtration, where fatty acid salts can be separated.

When the separation treatment is a distillation and when a crude glycerol-based product according to the invention is used for the manufacture of dichloropropanol, the dichloropropanol separated can be contaminated by various isomers of chloroalkoxypropanol or of dialkoxypropanol. The chloroalkoxypropanol or dialkoxypropanol isomers are preferably those for which the alkoxy group is chosen from the methoxy, ethoxy, propoxy, butoxy, pentoxy, hexoxy, heptoxy and octoxy groups, preferably from the methoxy, ethoxy, propoxy and butoxy groups, more preferably from the methoxy and ethoxy groups. The alkoxy group is very particularly preferably the methoxy group. The propoxy group is chosen from n-propoxy, isopropoxy group and mixture thereof, and is preferably an isopropoxy group. The butoxy group is chosen from 1-butoxy, 2-butoxy, isobutoxy, tert-butoxy group, and mixtures of least two of them, and is preferably an isobutoxy or a tertbutoxy group. The treatment of the crude glycerol-based product according to the invention exhibits the advantage of reducing the contamination of the dichloropropanol by these isomers.

Finally, the invention relates to a process for the manufacture of epichlorohydrin comprising the process for the manufacture of dichloropropanol starting from glycerol in which a crude glycerol-based product is subjected to at least one treatment, optionally under reduced pressure, of evaporative concentration, of evaporative crystallization, of distillation, of fractional distillation, of stripping or of liquid-liquid extraction so as to reduce the content of the glycerol alkyl ethers and to obtain a purified glycerol-based product which is reacted with a chlorinating agent, followed by a process for the dehydrochlorination of dichloropropanol.

When the dichloropropanol is contaminated by various isomers of chloroalkoxypropanol, the epichlorohydrin can be contaminated by alkyl glycidyl ethers. The alkyl glycidyl ethers are preferably those for which the alkyl group is chosen from the methyl, ethyl, propyl, butyl, pentyl, hexyl, heptyl and octyl groups, preferably from the methyl, ethyl, propyl and butyl groups, more preferably from the methyl and ethyl groups. The alkyl group is very particularly preferably the methyl group. The propyl group is chosen from n-propyl, isopropyl group and mixture thereof, and is preferably an isopropyl group. The butyl group is chosen from 1-butyl, 2-butyl, isobutyl, tert-butyl group, and mixtures of least two of them, and is preferably an isobutyl or a tertbutyl group. This contamination can be reduced by using a dichloropropanol manufactured from the purified glycerol-based product according to the invention. These alkyl glycidyl ethers exhibit boiling points very close to that of epichlorohydrin and are, for this reason, very difficult to separate from it.

In the process for preparing epichlorohydrin according to the invention, the dichloropropanol may be subjected to a dehydrochlorination reaction as described in WO 2005/054167, the content of which is incorporated herein by reference, especially the passages from page 19, line 12, to page 22, line 30 and WO 2006/100311, of SOLVAY SA, the content of which is incorporated herein by reference, especially the passages from page 2, line 22 to 25, and from page 22, line 27, to page 23, line 32.

The dehydrochlorination of dichloropropanol may also be carried out as described in WO 2006/100318 of SOLVAY SA, the content of which is incorporated here by reference, especially the passages from page 2, line 23 to 28, and from page 24, line 17, to page 32, line 3.

The process for preparing dichloropropanol according to the invention, may be integrated within an overall plan for preparation of epichlorohydrin, as described in the WO 2006/106155 of SOLVAY SA, the content of which is incorporated here by reference, especially the passages from page 2, line 26 to page 31, and from page 21, line 18, to page 23, line 6.

Finally, the invention relates to a process for the manufacture of epoxy resins comprising a process for the manufacture of epichlorohydrin by dehydrochlorination of dichloropropanol, obtained by chlorination of a purified glycerol-based product, in which epichlorohydrin is subjected to a reaction with a compound containing at least two active hydrogen atoms. These compounds include polyphenolic compounds, mono- and diamines, amino phenols, heterocyclic imides and amides, aliphatic diols and polyols, and dimeric fatty acids.

The examples below are intended to illustrate the invention without, however, limiting it.

EXAMPLE 1

A crude glycerol resulting from the manufacture of biodiesel by a process for the transesterification of rapeseed oil by methanol in the presence of a heterogeneous catalyst and operated under conditions such that ethers of glycerol have formed and have not been separated from glycerol, has been obtained. Such conditions are for example, the use of an acidic heterogeneous catalyst, the presence of acidic compounds, for instance carboxylic acids in the colza oil, a high transesterification temperature and a long residence time of the mixture methanol/soja oil on the catalyst. That crude glycerol was distilled under reduced pressure. The operation was carried out in an arrangement composed of a round-bottomed flask equipped with a pocket having a thermocouple, with a magnetic bar for the stirring, with a distillation head with a pocket having a thermocouple, with a side reflux condenser cooled to 0° C. and with a round-bottomed flask for collecting the evaporate. The compounds not collected in the round-bottomed flask were condensed in a trap cooled to −78° C. The water and the methanol were distilled at first under a reduced pressure of 9 torr at ambient temperature. Fractions enriched in glycerol methyl ethers were subsequently collected at a constant pressure of 3 torr with a boiling point of the mixture of 159-160° C. and a measured vapour temperature of 151-155° C. Three distillate fractions were collected. The contents of various compounds of the crude glycerol (crude glycerol-based product), of the fractions collected, of the trap and of the distillation residue (purified glycerol-based product) are given in Table 1 below.

TABLE 1

|  | Crude glycerol-based product | Fraction 1 | Fraction 2 | Fraction 3 | Trap | Purified glycerol-based product |
| --- | --- | --- | --- | --- | --- | --- |
| Amount (in g) | 100.09 | 4.00 | 3.78 | 5.02 | 1.98 | 83.26 |
| Constituents (in g/kg) | | | | | | |
| methanol | 2.4 | | 0.006 | 0.009 | 0.035 | 0.008 |
| ethanol | 0.014 | | | | | |
| propanol | 0.016 | | | | | |
| ethylene glycol | 0.22 | 2.2 | 0.22 | 0.088 | 5.4 | 0.02 |
| propylene glycol | 0.14 | 0.85 | 0.056 | 0.024 | 10 | |
| 2 methoxypropanediol isomers | 11.3 | 176 | 36 | 11.7 | 36.7 | 0.9 |
| glycerol | 965 | 744 | 957 | 981 | 37 | 992 |
| glycerol monoacetate | 0.35 | 1.4 | 1.1 | 0.71 | 0.12 | 0.21 |
| 3 diglycerol isomers | 2.8 | 0.01 | 0.096 | 1.1 | | 3.4 |
| methyl oleate + methyl linoleate | 6.8 | 78 | 1.8 | 0.04 | | <0.001 |
| glycerol monooleate + glycerol monolinoleate | 3.9 | 1.1 | 0.92 | 1.8 | | 2.2 |
| water | 6.8 | 1.4 | 0.4 | 0.5 | | 0.2 |

EXAMPLE 2

A crude glycerol resulting from the manufacture of biodiesel by a process for the transesterification of rapeseed oil by methanol in the presence of a heterogeneous catalyst and operated under conditions such that ethers of glycerol have formed and have not been separated from glycerol, has been obtained. Such conditions are for example, the use of an acidic heterogeneous catalyst, the presence of acidic compounds, for instance carboxylic acids in the colza oil, a high transesterification temperature and a long residence time of the mixture methanol/soja oil on the catalyst. That crude glycerol was treated with steam under reduced pressure. The operation was carried out in an arrangement composed of a round-bottomed flask equipped with a pocket having a thermocouple, with a magnetic bar for the stirring, with a dip pipe for the injection of steam, with a distillation head with a pocket having thermocouple, with a side reflux condenser cooled to 0° C. and with a round-bottomed flask for collecting the evaporate. The compounds not collected in the round-bottomed flask were condensed in a trap cooled to −78° C. Steam at 140° C. (33.19 g) was injected in 63 minutes. The condensate was collected under a constant pressure of 26 torr with a boiling point of the mixture of 127-139° C. and a measured vapour temperature of 91-97° C. The contents of various compounds of the crude glycerol (crude glycerol-based product) and of the stripping residue (purified glycerol-based product) are given in the following Table 2.

TABLE 2

| | Crude glycerol-based product | Purified glycerol-based product |
|---|---|---|
| Amount (in g) | 148.6 | 141.64 |
| Constituents (in g/kg) | | |
| water | 6.8 | 4.9 |
| methanol | 2.4 | 0.017 |
| ethanol | 0.014 | <0.005 |
| propanol | 0.016 | <0.005 |
| ethylene glycol | 0.22 | 0.03 |
| propylene glycol | 0.14 | <0.001 |
| 2 methoxypropanediol isomers | 11 | 3.9 |
| glycerol | MC(960-965) | MC (994) |
| glycerol monoacetate | 0.35 | 0.37 |
| 3 diglycerol isomers | 2.8 | 2.9 |
| methyl oleate + methyl linoleate | 6.8 | <0.001 |
| glycerol monooleate + glycerol monolinoleate | 3.9 | 1.7 |

MC = Main constituent

The invention claimed is:

1. A process for the manufacture of dichloropropanol comprising reacting a glycerol-based product comprising at least 500 g of glycerol per kg of product and glycerol alkyl ethers in an amount of 0.001 to 5 g/kg of product with a chlorinating agent to produce dichloropropanol.

2. The process according to claim 1, wherein the glycerol-based product comprises glycerol alkyl ethers in an amount of 0.001 to 1 g/kg of product.

3. The process according to claim 1, wherein the glycerol alkyl ethers are glycerol monoethers, glycerol diethers, glycerol triethers, or mixtures thereof, the alkyl groups of said glycerol alkyl ethers being selected independently from the group consisting of methyl, ethyl, propyl, butyl, pentyl, hexyl, heptyl, and octyl groups.

4. The process according to claim 1, wherein the glycerol alkyl ethers are selected from the group consisting of glycerol monomethyl ethers, monoethyl ethers, and mixtures thereof.

5. The process according to claim 1, wherein the glycerol-based product has one or more of the following features:

the glycerol alkyl ethers are methyl ethers;

said product comprises methanol in an amount of 0.1 to 20 g/kg of product;

said product comprises ethanol, propanol, butanol, pentanol, hexanol, heptanol, octanol, ethylene glycol and propylene glycol in a total amount of 0.01 to 2 g/kg of product;

the glycerol alkyl ethers are ethyl ethers;

said product comprises ethanol in an amount of 0.1 to 20 g/kg of product;

said product comprises methanol, propanol, butanol, pentanol, hexanol, heptanol, octanol, ethylene glycol and propylene glycol in a total amount of 0.01 to 2 g/kg of product;

the glycerol alkyl ethers are propyl ethers;

said product comprises propanol in an amount of 0.1 to 20 g/kg of product; and said product comprises methanol, ethanol, butanol, pentanol, hexanol, heptanol, octanol, ethylene glycol and propylene glycol in a total amount of 0.01 to 2 g/kg of product.

6. The process according to claim 1, further comprising subjecting product to at least one treatment, optionally under reduced pressure, selected from the group consisting of evaporative concentration, evaporative crystallization, distillation, fractional distillation, stripping, and liquid-liquid extraction prior to being reacted with a chlorinating agent to produce dichloropropanol.

7. The process according to claim 6, wherein a purified glycerol-based product is obtained by said treatment and reacted with a chlorinating agent to produce dichloropropanol, said purified glycerol-based product comprising glycerol alkyl ethers in an amount of less than 5 g/kg of purified product and methanol, ethanol, propanol, butanol, pentanol, hexanol, heptanol, octanol, ethylene glycol and propylene glycol in a total amount of less than 1 g/kg of purified product.

8. The process according to claim 7 wherein the glycerol alkyl ethers are selected from the group consisting of glycerol methyl ethers, glycerol ethyl ethers, glycerol propyl ethers, glycerol butyl ethers, and any mixtures of at least two of them.

9. The process according to claim 8, wherein said purified glycerol-based product presents one or more of the following features:

said purified glycerol-based product comprises glycerol methyl ethers in an amount of less than 5 g/kg of purified product;

said purified glycerol-based product comprises glycerol ethyl ethers in an amount of less than 5 g/kg of purified product;

said purified glycerol-based product comprises glycerol propyl ethers in an amount of less than 5 g/kg of purified product; or said purified glycerol-based product comprises methanol, ethanol, propanol, butanol, ethylene glycol and propylene glycol in a total amount of less than 1 g/kg of purified product.

10. The process according to claim 1, wherein the alkyl ethers are methyl ethers or ethyl ethers.

11. The process according to claim 1, further comprising dehydrochlorination of the dichloropropanol to produce epichlorohydrin.

12. The process according to claim 11, further comprising subjecting the epichlorohydrin to a reaction with a compound comprising at least two active hydrogen atoms to produce an epoxy resins.

13. The process according to claim 1, wherein the glycerol alkyl ethers are glycerol monomethyl ethers.

14. The process according to claim 2, further comprising dehydrochlorination of the dichloropropanol to produce epichlorohydrin.

15. The process according to claim 14, further comprising subjecting the epichlorohydrin to a reaction with a compound comprising at least two active hydrogen atoms to produce an epoxy resins.

16. The process according to claim 1, wherein the glycerol-based product comprises at least 750 g of glycerol per kg of product and glycerol alkyl ethers in an amount of 0.01 to 0.5 g/kg of product.

17. The process according to claim 1, wherein the glycerol-based product comprises at least 990 g of glycerol per kg of product and glycerol alkyl ethers in an amount of 0.1 to 5 g/kg of product.

* * * * *

UNITED STATES PATENT AND TRADEMARK OFFICE
CERTIFICATE OF CORRECTION

PATENT NO. : 8,124,814 B2
APPLICATION NO. : 12/304391
DATED : February 28, 2012
INVENTOR(S) : Philippe Krafft et al.

Page 1 of 1

It is certified that error appears in the above-identified patent and that said Letters Patent is hereby corrected as shown below:

Column 16, line 62, "epoxy resins." should read --epoxy resin.--

Column 17, line 4, "epoxy resins." should read --epoxy resin.--

Signed and Sealed this
First Day of May, 2012

David J. Kappos
*Director of the United States Patent and Trademark Office*